US00PP25128P3

(12) United States Plant Patent
Slaughter et al.

(10) Patent No.: US PP25,128 P3
(45) Date of Patent: Dec. 2, 2014

(54) NECTARINE TREE, 'BURNECTTWENTYSEVEN'

(50) Latin Name: ***Prunus persica* (subspecies *nucipersica*)**
Varietal Denomination: Burnecttwentyseven

(71) Applicants: John K. Slaughter, Fresno, CA (US); Timothy J. Gerdts, Kingsburg, CA (US)

(72) Inventors: John K. Slaughter, Fresno, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 167 days.

(21) Appl. No.: 13/694,712

(22) Filed: Dec. 26, 2012

(65) Prior Publication Data
US 2014/0182022 P1 Jun. 26, 2014

(51) Int. Cl.
*A01H 5/00* (2006.01)

(52) U.S. Cl.
USPC ..... Plt./189

(58) Field of Classification Search
USPC ..... Plt./189
See application file for complete search history.

*Primary Examiner* — Kent L Bell
(74) *Attorney, Agent, or Firm* — Paine Hamblen, LLP

(57) ABSTRACT

A new and distinct variety of nectarine tree, denominated varietally as 'Burnecttwentyseven', and which produces an attractively colored white-fleshed, sub-acid freestone nectarine, which is mature for harvesting and shipment approximately August 20 to 28 under ecological conditions prevailing in the San Joaquin Valley of central California.

2 Drawing Sheets

Botanical designation: The present invention relates to a new, novel and distinct variety of nectarine tree *Prunus persica* (subspecies *nucipersica*).

Varietal denomination: 'Burnecttwentyseven'.

BACKGROUND OF THE NEW VARIETY

The present variety of nectarine tree resulted from an ongoing program of fruit and nut tree breeding. The purpose of this program is to improve the commercial quality of available deciduous fruit and nut varieties, and rootstocks, by creating and releasing promising selections of *Prunus, Malus* and *Regia* species. To this end we make both controlled and hybrid cross pollinations each year in order to produce seedling populations from which improved progenies are evaluated and and distinct variety of nectarine tree, which is considered of large size, and which has selected.

The seedling 'Burnecttwentyseven' was originated by us from a population of seedlings grown in our experimental orchards which are located near Fowler, Calif. The seedlings, grown on their own roots, were the result of a controlled cross made by us in 2005 using the nectarine tree 'Burnecttwentyone' (U.S. Plant Pat. No. 17,233), which was used as the seed parent; and an un-named white-fleshed nectarine tree which was used as the pollen parent. One seedling, Q62.081, which is the present variety, exhibited especially desirable characteristics, and was marked for subsequent observation. After the 2007 fruiting season, the new, present variety, was selected for advanced evaluation and repropagation.

ASEXUAL REPRODUCTION

Asexual reproduction of the new and distinct variety of nectarine tree was accomplished by budding the new nectarine tree on to 'Nemaguard' Rootstock (non-patented). This was performed by us in our experimental orchard which is located near Fowler, Calif. Subsequent evaluations have shown those asexual reproductions run true to the original tree. All characteristics of the original tree, and its fruit, were established, and appear to be transmitted through succeeding asexual propagations. We have observed fruit for the past 4 successive years from approximately 15 propagated trees.

SUMMARY OF THE VARIETY

'Burnecttwentyseven' is a new vigorous growth. This new nectarine tree variety is also a regular and productive bearer of relatively large, firm, non-acid white-fleshed, melting, freestone fruit which have good flavor and eating quality. The tree of the present variety displays a medium chilling requirement of approximately 650 hours. Still further, the present tree also produces relatively uniformly sized fruit throughout the tree. Additionally, the fruit produced by the present tree has a high degree of red skin coloration, a firm flesh and appears to have good handling and shipping qualities. The 'Burnecttwentyseven' Nectarine tree bears fruit which are ripe for commercial harvesting and shipment on approximately August 20 to August 28 under the ecological conditions prevailing in the San Joaquin Valley of central California. In relative comparison to the seed parent nectarine tree, 'Burnecttwentyone', the present new variety ripens approximately 7-10 days earlier. In relative comparison to the nectarine tree, 'Regal Pearl' tree (U.S. Plant Pat. No. 17,254), which is the most similar commercial variety known to the breeders at this time, the fruit of the new, present, variety is (approximately 8-10 millimeters) larger. Further, the fruit new of the new variety, when compared to the fruit of the 'Regal Pearl' (U.S. Plant Pat. No. 17,254) ripens 4-6 days later. In relative comparison to the new variety, the pollen parent yields fruit than ripen on or about July 5. This ripening date is approximately 6 weeks earlier than the new variety.

BRIEF DESCRIPTION OF THE DRAWINGS

The accompanying drawings, which are provided, include two color photographs of the new variety of nectarine tree.

Figure 1:
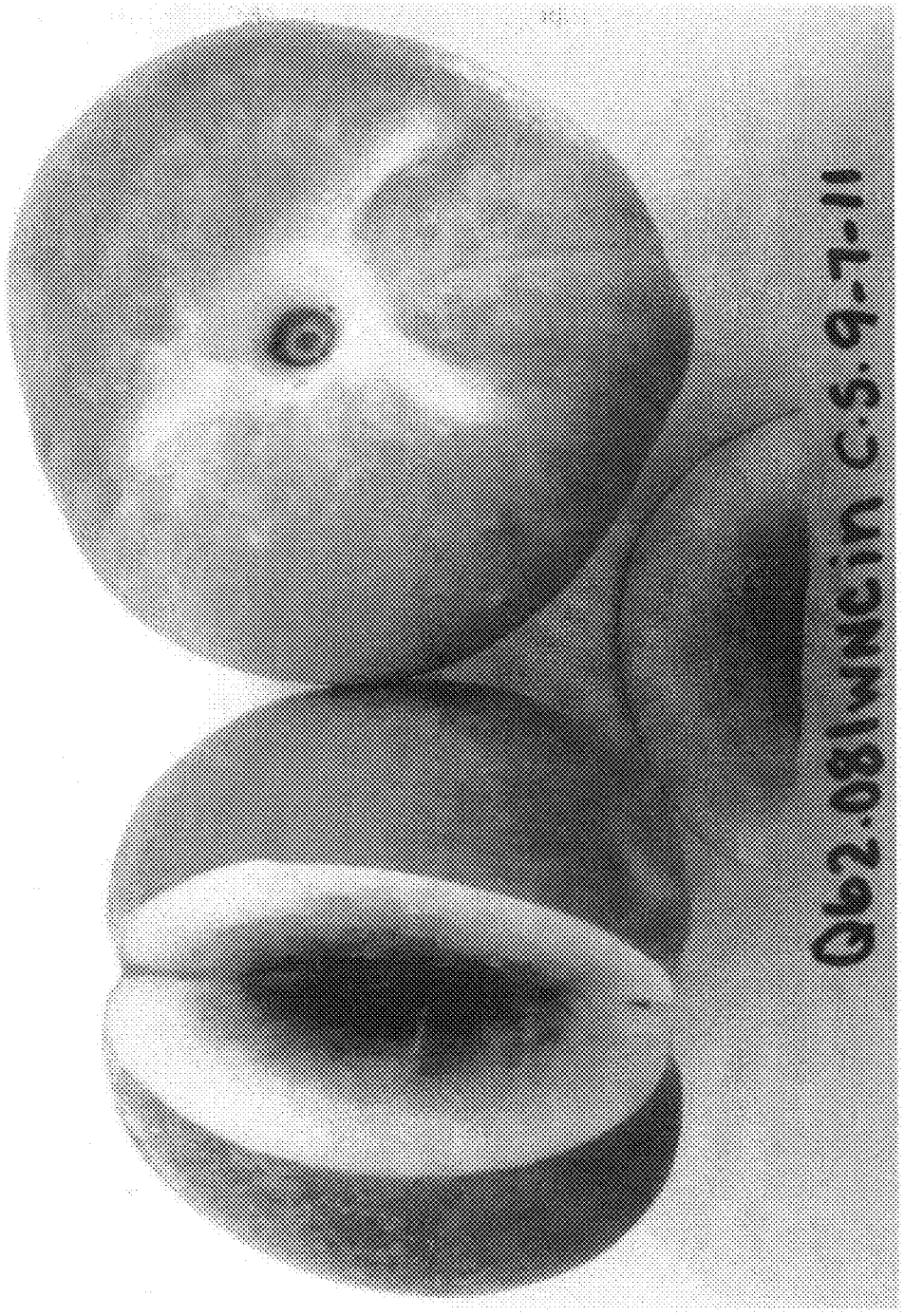
FIG. 1 depicts two whole mature fruit, one of which displays a fruit viewed from the basal aspect, and one of which is dissected substantially in the sagital plane and viewed from the lateral perspective, revealing the flesh characteristics thereof. Additionally the segment of fruit removed from the aforementioned dissection is presented to further display the internal coloration of the fruit at full commercial maturity. The external coloration of the fruit, as shown, is sufficiently matured for harvesting and shipment.

The colors in these photographs are as nearly true as is reasonably possible in a color representation of this type. Due to chemical development, processing, and printing, the leaves and fruit depicted in these photographs may or may not be accurate when compared to the actual specimen. For this reason, future color references should be made to the color plates (Royal Horticultural Society, Fourth Edition, 2001) and descriptions provided.

NOT A COMMERCIAL WARRANTY

The following detailed description has been prepared to solely comply with the provisions of 35 U.S.C. §112, and does not constitute a commercial warranty, (either expressed or implied), that the present variety will in the future display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of nectarine tree, the following has been observed during the sixth fruiting season under the ecological conditions prevailing at orchards which are located near the town of Fowler, county of Fresno, state of Calif. All major color code designations are by reference to The R.H.S. Colour Chart (Fourth Edition) and which is provided by The Royal Horticultural Society of Great Britain. Common color names are also occasionally used.

TREE

*Size.*—Generally. — Considered medium-large as compared to other common commercial nectarine cultivars ripening in the early season of maturity. The tree of the present variety was pruned to a height of approximately 280.0 cm to about 320.0 cm at commercial maturity.

*Tree height.*—3.8 meters.

*Canopy width.*—3.7 meters.

*Vigor.*—Considered vigorous. The present variety grew from about 200.0 cm to 210.0 cm, in height, during the first growing season. The new nectarine tree variety was pruned to a height of approximately 150.0 cm during the first dormant season, and primary scaffolds were then selected for the desired tree structure.

*Productivity.*—Productive. Fruit set varies from 1.5, to several times more than the desired crop load. Fruit set is spaced by thinning to develop the remaining fruit into the desired market sized fruit. The number of the fruit set varies with prevailing climatic conditions, and the cultural practices employed during the bloom period, and is therefore not a distinctive characteristic of this new variety.

*Fruit bearing.*—Regular. Fruit set has been moderate, and some thinning was necessary during the past 4 years.

*Tree form.*—Upright, and pruned to a vase shape.

*Tree density.*—Considered medium dense. It has been discovered that pruning the branches from the center of the tree to obtain a resulting vase shape allows for proper air movement in the tree, and appropriate amounts of sunlight to enhance fruit color and renewal of fruiting wood throughout the tree.

*Hardiness.*—The present tree was grown and evaluated in USDA Hardiness Zone 9.

*Winter chilling requirements.*—The new tree requires approximately 650 hours of chilling below 7.0 degrees C. The variety appears to be hardy under typical Central San Joaquin Valley climatic conditions.

TRUNK

*Diameter.*—Approximately 18.0 cm in diameter when measured at a distance of approximately 15.24 cm above the soil level, and at the end of the sixth growing season.

*Bark texture.*—Considered moderately rough, with numerous folds of papery scarfskin being present.

*Lenticels.*—Numerous flat, oval lenticels are present. The lenticels range in size from approximately 3.0 to about 6.0 millimeters in width, and from about 1.0 to about 2.0 millimeters in height. It should be noted that as the cork (bark) of trees mature the lenticels become less apparent and less abundant.

*Lenticel color.*—Considered an Orange Brown, (RHS Greyed-Orange Group 164 C).

*Bark coloration.*—Variable, but it is generally considered to be grey-brown, (RHS Grey-Brown Group N199 C).

BRANCHES

*Size.*—Considered medium large for the variety.

*Diameter.*—Average as compared to other nectarine tree varieties. The branches of the present variety have a diameter of about 7.0 centimeters when measured during the fourth year after grafting.

*Surface texture.*—Average, and appearing furrowed on wood which is several years old.

*Crotch angles.*—Primary branches are considered variable between about 45 degrees to about 55 degrees from the horizontal axis. This particular characteristic is not considered distinctive of the variety, however.

*Current season shoots.*—Surface texture — Substantially glabrous.

*Internode length.*—Approximately 2.3 cm. to about 2.5 cm. This tree characteristic is highly dependent upon plant nutrition, soil quality, pruning and general tree care, and therefore is not a particularly distinctive characteristic of the new variety.

*Color of mature branches.*—Medium brown, (RHS Greyed-Orange 165 A).

*Current seasons shoots.*—Color — Light green, (RHS Yellow-Green Group 144 B). The color of new shoot tips is considered a bright and shiny green (RHS Green Group 143 B).

LEAVES

*Size.*—Considered medium large for the species. Leaf measurements have been taken from vigorous, upright, current-season growth, at approximately mid-shoot.

*Leaf length.*—Approximately 141.0 to about 155.0 millimeters.

*Leaf width.*—Approximately 32.0 to about 39.0 millimeters.

*Leaf base shape.*—Slightly oblique relative to the leaf longitudinal axis.

*Leaf form.*—Lancelolate.

*Leaf tip form.*—Acute.

*Leaf color.*—Upper surface — Medium green, (approximately RHS Green Group 137 B).

*Leaf texture.*—Glabrous.

*Leaf color.*—Lower Surface — Medium green, (RHS Green Group 143 A).

*Leaf venation.*—Pinnately veined.

*Mid-vein.*—Color. — Light yellow green, (RHS Yellow-Green Group 150 C).

*Leaf margins.*—Slightly undulating. Form. — Considered crenate, occasionally doubly crenate. Uniformity. — Considered generally uniform.

*Leaf petioles.*—Size. — Considered medium long. Length. — about 8.0 mm. to about 11.0 mm. Diameter. — about 2.0 mm. to about 2.5 mm. Color. — Pale green, (RHS Yellow-Green Group 144 A).

*Leaf glands.*—Size. — About 1.0 mm. in height, and about 1.0 mm. in width. Number. — Generally two per side, occasionally one per side. Type. — Globose, and considered reasonably unappressed to the petiole margin and moderately small. The glands on more mature leaves are occasionally senescent. Color. — Orange brown, (RHS Greyed-Orange Group 177 A).

*Leaf stipules.*—Size. — Medium for the variety. Length. — Approximately 8.0 mm.-11.0 mm. Width. — Approximately 1.0mm.-1.5 mm. Number. — Typically 2 per leaf bud, and up to 6 per shoot tip. Form. — Lanceolate in form, and having a serrated margin. Color. — Green, (RHS Green Group 139 A) when young, but graduating to a brown color, (RHS Greyed-Orange group 177 A), with advancing senescence. The stipules are considered to be early deciduous.

FLOWER BUDS

*Flower buds.*—Generally — The floral buds, depending upon the stage of development, are approximately 7.0 millimeters wide; and about 15.0 millimeters long; conic in form; and slightly appressed relative to the bearing shoot.

*Flower bud scales.*—Color — The bud scales are reddish-brown, (approximately RHS Greyed-Purple Group 183 B). The flow buds, generally speaking, are considered hardy under typical central San Joaquin Valley climatic conditions.

*Hardiness.*—No winter injury has been noted during the last several years of evaluation in the central San Joaquin Valley. The current variety has not been intentionally subjected to drought or heat stress, and therefore this information is not available. The current variety is considered to have a medium chilling requirement for the region in which it is presently growing. It is possible to experience frost damage on either flowers or small fruit due the early initiation of the blooming period and exposure to damaging temperatures during the late winter months after the bloom.

FLOWERS

*Blooming time.*—Considered mid-season in relative comparison to other commercial nectarine cultivars grown in the central San Joaquin Valley.

*Date of first bloom.*—Feb. 28, 2012.

*Date of full bloom.*—This was observed on Mar. 4, 2012. The date of bloom varies slightly with the prevailing climatic conditions, and cultural practices which were employed.

*Duration of bloom.*—Approximately 10 days. This characteristic varies slightly with the prevailing climatic conditions.

*Flower class.*—Perfect, complete and perigynous.

*Flower type.*—The variety is considered to have a showy type flower.

*Flower size.*—Flower diameter at full bloom is approximately 38.0 to about 44.0 millimeters.

*Bloom quantity.*—Considered very abundant.

*Flower bud frequency.*—Normally 2 flower buds appear per node. On very rare occasions, 3 buds per node may be observed.

*Petal size.*—Generally — Considered large for the species. Length. — Approximately 18.0 to about 22.0 millimeters. Width. — Approximately 17.0 to about 21.0 millimeters.

*Petal form.*—Rotund to slightly ovate.

*Petal count.*—Generally 5. Occasionally individual flower pedal counts are doubled.

*Petal texture.*—Glabrous.

*Petal color.*—Upper Surface — Light pink, (RHS Red-Purple Group 62 D), to a medium pink, (RHS Red-Purple Group N57 C); Lower surface — Very light pink (RHS Red-Purple Group 69C).

*Fragrance.*—Slight.

*Petal claw.*—Form. — The claw is considered truncate in shape, and generally has a medium size when compared to other known varieties. Length. — Approximately 9.0 mm. to about 11.0 mm. Width. — Approximately 10.0 mm. to about 12.0 mm.

*Petal margin shapes.*—Generally considered variable, from nearly smooth, to moderately undulate.

*Petal apex.*—Generally — The petal apices generally appear entire with a small, narrow apical groove; Size — approximately 1.0-2.0 mm in length, and approximately 1.0 mm in width; Petal Base — Generally rounded to slightly truncate.

*Flower pedicel.*—Length. — Considered medium-long, and having an average length of approximately 5.0 mm. to about 6.0 mm. Diameter. — Considered average, approximately 2.0mm.-3.0 mm. Color. — A medium-light green, (RHS Yellow Green Group 144 A).

*Floral nectaries.*—Color. — An orange brown, (RHS Greyed-Orange Group N172 A).

*Calyx.*—Surface Texture. — Generally glabrous. Color. — Lower Surface — A dull red, (approximately RHS Greyed-Red Group 178 B); Upper Surface — a dull red (RHS Greyed-Red Group 183A).

*Sepals.*—Surface Texture. — The surface has a short, fine, pubescent texture. Number. — Always five. Size. — Average, and ovate in form. Sepal Length. — Approximately 7.0 mm. to 8.0 mm. Sepal Width. — Approximately 6.0 mm. to 7.0 mm. Sepal Shape. — A single entire lobe. Nearly round. Sepal Margin. — Smooth, entire. Sepal Color. — Upper and Lower Surfaces — A dark reddish purple, (approximately RHS Greyed-Purple Group 183 A).

*Anthers.*—Generally. — Large in size, approximately 11-14 millimeters in length; and 1 millimeter in width. Color. — Red to reddish purple, (approximately RHS Greyed-Purple Group 185 A) prior to dehiscence.

*Pollen production.*—Pollen is abundant, and has a yellow color, (approximately RHS Yellow Group 12 B).

*Fertility.*—Self fertile.

*Filaments.*—Size. — Variable in length, approximately 12.0 to about 17.0 millimeters in length. Color. — Considered a pale pink, (RHS White Group N155 B) to a medium-dark pink (RHS Red-Purple Group 65 A) as the flower matures and begins to dehisce.

*Pistil.*—Number. — Normally 1, rarely 2. Generally. — Average in size. Length. — Approximately 19.0 to about 23.0 millimeters including the ovary. Color. — Considered a very pale green, (approximately RHS Yellow-Green Group 145 C). Surface Texture. — The variety has a long glabrous pistil.

FRUIT

*Maturity when described.*—Firm ripe condition (shipping ripe). Date of first picking. — approximately Aug. 20, 2007. Date of last picking. — Aug. 30, 2007. The date of harvest varies slightly with climatic conditions and the prevailing cultural practices.

*Size.*—Generally — Considered large, and uniform.

*Average cheek diameter.*—Approximately 72.0 mm. to about 79.0 mm.

*Average axial diameter.*—Approximately 70.0 mm. to about 74.0 mm.

*Typical weight.*—Approximately 270.0 grams. This characteristic is highly dependent upon the prevailing cultural practices, and therefore is not particularly distinctive of this new variety.

*Fruit form.*—Generally — Rounded to oblate. The fruit is generally uniform in symmetry.

*Fruit suture.*—Shallow, and extending from the stem well to the apex. No apparent callousing or stitching exists along the suture line.

*Suture.*—Color — The background color appears to be white, (approximately RHS Yellow-Orange Group 15 B), with occasional red coloration, appearing, (approximately RHS Red Group 46 A).

*Ventral surface.*—Form — Full.

*Apex shape.*—Rounded.

*Base.*—Form — Generally retuse.

*Stem cavity.*—Shape — Rounded and relatively shallow. The average depth of the stem cavity is about 1.2 cm. The average width of the stem cavity is about 1.85 cm.

*Fruit skin.*—Thickness. — Considered medium in thickness, and tenacious to the flesh. Surface Texture. — Glabrous. Taste. — Slightly astringent. Tendency to crack. — Cracking has not been observed. Further, russeting has not been observed to date.

*Fruit skin color.*—Blush Color. — The blush color is variable from a medium red, (approximately RHS Red Group 42 A), to a dark red, (approximately RHS Red Group 46 A). The blush color ranges from 85% to about 95% of the fruit surface depending upon the sunlight exposure, and the prevailing growing conditions.

*Ground color.*—Generally a light yellow, (approximately RHS Yellow Group 8 B).

*Fruit stem.*—Moderate in length, approximately 6.0 mm. to about 9.0 mm. Diameter. — Approximately 2.0 mm. to about 3.0 mm. Color. — Medium-dark brown, (approximately RHS Greyed-Orange Group 175 A).

*Fruit flesh.*—Ripens. — Evenly. Texture. — Firm, and dense. Considered melting. Fibers. — Few, small, and tender ones are found. Aroma. — Slight. Eating Quality. — Considered good. Flavor. — Considered sweet with a hint of acid. The flavor is considered pleasant. Acid. — Considered a sub-acidic fruit. Approximately 0.3 titratable acidity was detected. Juice Production. — Moderate. Brix. — About 15.5 degrees. This characteristic varies slightly with the number of fruit per tree; the prevailing cultural practices; and the surrounding climatic conditions. Flesh Color. — Considered white in color, and having a very pale yellow tint, (approximately RHS Yellow 11 D).

STONE

*Type.*—A tight free stone.

*Size.*—Considered medium for the variety. The stone size varies with the resulting crop load, and tree vigor, and is therefore is not considered a distinguishing characteristic of this new variety.

*Length.*—Average, about 37.0 mm. to about 40.0 mm.

*Width.*—Average, about 28.0 mm. to about 30.0 mm.

*Diameter.*—Average, about 19.0 mm. to about 22.0 mm.

*Stone form.*—Ovoid.

*Stone base.*—The stone is slightly oblique relative to the stone's vertical axis.

*Apex.*—Shape — The stone apex has a small raised tip.

*Stone surface.*—Surface Texture — Substantial pitting is evident, in general, from the base to a location past the equatorial plane. Grooving is usually observed along the pit margin, near the tip, and on the ventral side. Ridges. — Shape — The surface texture varies from sharp to rounded. Ventral Edge. — Width — Considered medium, and having a dimension of approximately 3.0 mm. to about 4.0 mm. when measured at the mid-suture. Dorsal Edge. — Shape — Full, heavily grooved, and having relatively smooth edges.

Figure 2:
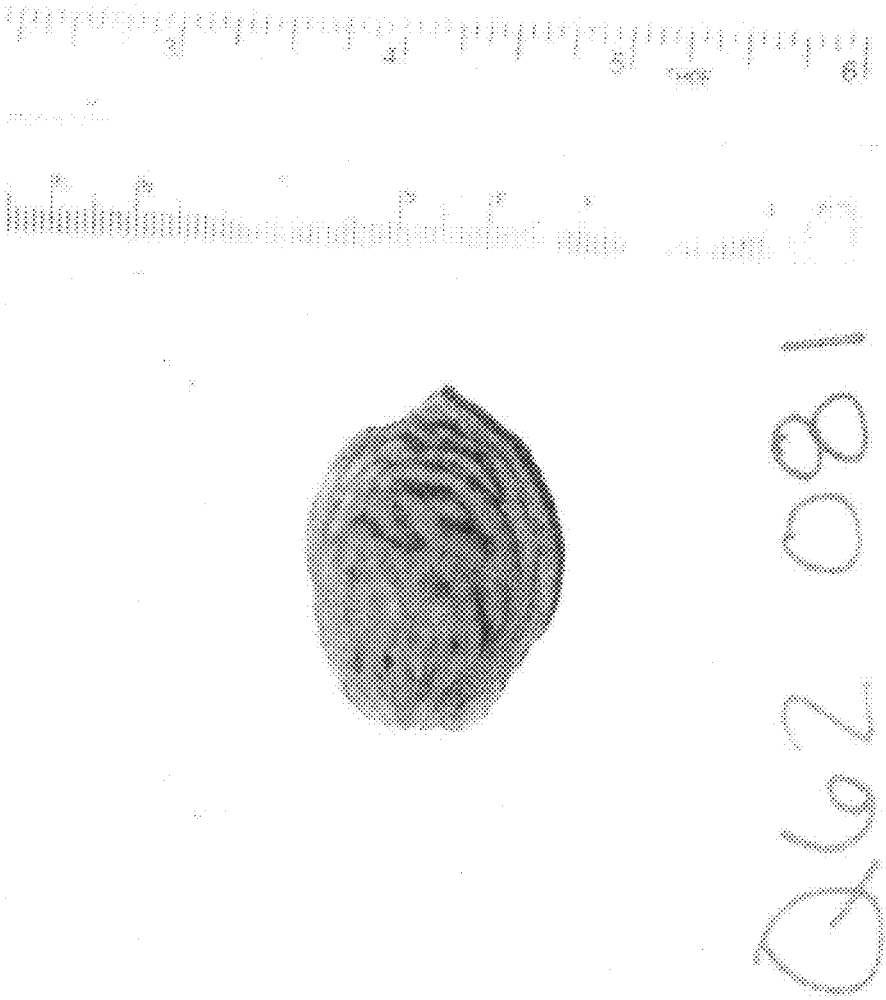
FIG. 2 depicts a lateral view of the stone, and its associated characteristics.

*Stone color.*—The color of the dry stone is a medium brown (RHS Greyed-Orange Group approximately 177 A). The stone as seen in FIG. 2 is freshly exposed, and can exhibit darkening hues from oxidation.

*Tendency to split.*—Rarely, splits have been noted.

*Kernel.*—Generally — The kernel is considered immature, and semi-gelatinous. Length. — Approximately 18.0 millimeters. Width. — Approximately 12.0 millimeters. Form. — Considered ovoid. Pellicle. — Pubescent. Color. — Considered to be a burnt orange (RHS Greyed-Orange Group N167 A).

*Use.*—The subject variety 'Burnecttwentyseven' is considered to be a Nectarine tree which matures late in the season, and which produces fruit, which are considered firm, attractively colored, and which are useful for both local and long distance shipping.

*Keeping quality.*—Excellent. Fruit has stored well for up to 25 days after harvest at 1.0 degree Celsius.

*Shipping quality.*—Good. The fruit of the new nectarine tree variety showed minimal bruising of the flesh, or skin damage, after being subjected to normal harvesting and packing procedures.

*Resistance to insects and disease.*—No particular susceptibilities were noted. The present variety has not been tested to expose or detect any susceptibilities or resistances to any known plant and/or fruit diseases.

Although the new variety of nectarine tree possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety of nectarine tree, what we claim is new, and desire to secure by plant Letters Patent is:

1. A new distinct variety of nectarine tree, substantially as illustrated and described, and which is characterized principally as to novelty by producing an attractively colored, white-fleshed, sub-acid freestone nectarine which is mature for harvesting and shipment approximately August 20 to August 28 under the ecological conditions prevailing in the San Joaquin Valley of central California.

* * * * *